United States Patent
Tanabe

(10) Patent No.: US 8,178,846 B2
(45) Date of Patent: May 15, 2012

(54) LIGHT OR RADIATION IMAGE PICKUP APPARATUS

(75) Inventor: Koichi Tanabe, Uji (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 13/054,948

(22) PCT Filed: Jul. 24, 2008

(86) PCT No.: PCT/JP2008/063259
§ 371 (c)(1),
(2), (4) Date: Jan. 20, 2011

(87) PCT Pub. No.: WO2010/010620
PCT Pub. Date: Jan. 28, 2010

(65) Prior Publication Data
US 2011/0127441 A1    Jun. 2, 2011

(51) Int. Cl.
*H01L 27/146* (2006.01)
(52) U.S. Cl. .................................................. 250/370.08
(58) Field of Classification Search ............ 250/370.01–370.15, 98.8
See application file for complete search history.

(56) References Cited

U.S. PATENT DOCUMENTS

| | | | | |
|---|---|---|---|---|
| 5,528,043 A | * | 6/1996 | Spivey et al. | 250/370.09 |
| 5,852,296 A | * | 12/1998 | Tsukamoto et al. | 250/370.09 |
| 5,886,353 A | * | 3/1999 | Spivey et al. | 250/370.09 |
| 5,970,115 A | * | 10/1999 | Colbeth et al. | 378/62 |
| 7,795,590 B2 | * | 9/2010 | Takahashi et al. | 250/363.03 |

FOREIGN PATENT DOCUMENTS

JP    2003-87656 A    3/2003

* cited by examiner

*Primary Examiner* — Kiho Kim
(74) *Attorney, Agent, or Firm* — Cheng Law Group, PLLC

(57) ABSTRACT

An X-ray detector provided for a radiation image pickup apparatus of this invention includes two types of areas, i.e. an image area for X-ray detection, and an image area for time variation noise detection to detect time variation noises generating from circuits of the X-ray detector. Consequently, time variation noises can be detected properly, regardless of damage to gate circuits of an active matrix substrate, by reading charge signals from the image area for time variation noise detection before a gate drive circuit is set to ON. As a result, a radiation image pickup apparatus with improved image quality can be manufactured.

8 Claims, 10 Drawing Sheets

LIGHT OR RADIATION IMAGE PICKUP APPARATUS

TECHNICAL FIELD

This invention relates to a light or radiation image pickup apparatus for use in the medical field or industrial field such as in non-destructive testing, RI (Radio Isotope) inspection and optical inspection, and more particularly to a technique for removing circuit noises of a detector that detects light or radiation.

BACKGROUND ART

Conventionally, a light or radiation image pickup apparatus has a light or radiation detector for detecting light or radiation. Light herein refers to infrared rays, visible light, ultraviolet rays, radiation, gamma rays and so on. An X-ray detector in particular will be described by way of example. As the X-ray detector, a flat panel detector (hereinafter called FPD) is in wide use which detects X-rays using an active matrix substrate. This is because the active matrix substrate is very useful in that X-ray detection values can be read on a pixel-by-pixel basis.

However, with the FPD using the active matrix substrate, time variation noises occurs as circuit noises. This is caused by noises or the like generating from wiring of the active matrix substrate or amplifier circuits. In order to remove these time variation noises, a method has been developed for removing the time variation noises from detection signals by calculating an average value of detection value, as time variation noises, acquired from areas at opposite ends of the FPD not used as pixels for X-ray detection, such as corrective pixel areas arranged in X-ray-shielded areas in a housing sealed with lead, for example.

As disclosed in Patent Document 1, for example, radiation shielding is made perfect in the corrective pixel areas at opposite ends of the FPD by disconnecting thin-film transistor (TFT) circuits and an X-ray conversion layer, to detect time variation noises generating from the TFT circuits, and wiring of the active matrix substrate and the amplifier circuits.

[Patent Document 1]
Unexamined Patent Publication No. 2003-87656

DISCLOSURE OF THE INVENTION

Problem to be Solved by the Invention

However, with the method disclosed in Patent Document 1, the TFT circuits and the radiation conversion layer must be disconnected in the corrective pixel areas at the opposite ends of the FPD, which forms a different step to an X-ray detecting area, requiring increased time and effort. When the TFT circuits in the corrective pixel areas have a defect, abnormal outputs of the TFT circuits will be detected as time variation noises. Further, since the TFT circuits and the radiation conversion layer must be disconnected, there arises a problem that X-ray detecting elements cannot be used as elements for correction.

This invention has been made having regard to the state of the art noted above, and its object is to provide a light or radiation image pickup apparatus which removes time variation noises accurately without being influenced by abnormal outputs of detecting elements sensitive to light or radiation in a corrective pixel area.

Means for Solving the Problem

To fulfill this object, this invention provides the following construction.

A light or radiation image pickup apparatus of this invention comprises a light or radiation detecting device having, arranged in a two-dimensional matrix form, a plurality of detecting elements for generating charge signals in response to light or radiation; a reading device for sending a switching signal to each row of the two-dimensional matrix of the light or radiation detection device for reading the charge signals; a charge-to-voltage converting device for converting the charge signals read from the light or radiation detection device on a row-by-row basis, into voltage signals on a column-by-column basis, respectively; a voltage signal holding device for sampling for a given time and holding for a predetermined time, on the column-by-column basis, the voltage signals converted by the charge-to-voltage converting device; an image processor for constructing a pickup image from the voltage signals held for the predetermined time by the voltage signal holding device; the detecting elements being divided into those arranged in a main pixel area and those arranged in a corrective pixel area within the light or radiation detection device; and a control device for performing controls to acquire corrective voltage signals by causing the voltage holding device to sample through the charge-to-voltage converting device, before the switching signal is sent, charge signals generated as different from those generated in response to the light or radiation, in a path extending from the detecting elements arranged in the corrective pixel area to the charge-to-voltage converting device, and to acquire main pixel detection signals by causing the voltage holding device to sample through the charge-to-voltage converting device, after the switching signal is sent, charge signals generated in the main pixel area; wherein the image processor forms a pickup image with time variation noises removed therefrom, using the main pixel detection signals and the corrective voltage signals.

According to the light or radiation image pickup apparatus of this invention, the timing of sampling the voltage signals from the detecting elements in the corrective pixel area is set to a time before the switching signal is sent. Thus, the corrective voltage signals can be measured without being influenced by charges generated by abnormal output of the detecting elements in the corrective pixel area, scattered light or scattered radiation. Consequently, the light or radiation image pickup apparatus provided can remove the time variation noises accurately.

The detecting elements in the corrective pixel area and the detecting elements in the main pixel area are different in the timing of sampling the voltage signals, which is either before or after the switching signal is sent. Therefore, the detecting elements in the main pixel area can be used as detecting elements in the corrective pixel area.

The image processor may include an offset signal removing unit for removing offset signals from the main pixel detection signals and the corrective voltage signals; a time variation noise first calculating unit for calculating row-by-row time variation noise average values which are average values for respective rows of the corrective signals with the offset signals removed therefrom; a time variation noise second calculating unit for calculating a time variation noise aggregate average value which is an average value for all rows of the row-by-row time variation noise average values; a time variation noise third calculating unit for calculating time variation noises for the respective rows by subtracting the time variation noise aggregate average value from the row-by-row time variation noise average values; and a time variation noise removing unit for subtracting the time variation noises for respective corresponding rows from the main pixel detection signals.

The above construction can calculate the time variation noises different from row to row with high precision, and remove the row-by-row time variation noises from the main pixel detection signals.

The image processor of alternative construction may include an offset signal removing unit for removing offset signals from the main pixel detection signals and the corrective voltage signals; a time variation noise first calculating unit for calculating row-by-row time variation noise average values which are average values for each respective rows of the corrective signals with the offset signals removed therefrom; a time variation noise second calculating unit for calculating a time variation noise block average value which is an average value for all rows from an nth row to an (n−m)th row, from the row-by-row time variation noise average values acquired for respective rows from the nth row to the mth row; a time variation noise third calculating unit for calculating a time variation noise for the nth row by subtracting the time variation noise block average value from the row-by-row time variation noise average value for nth row; and a time variation noise removing unit for subtracting the time variation noise for the nth row from the main pixel detection signals from the nth row; the above signal processing being carried out successively for the nth row, an n+1th row, an n+2th row, and so on.

According to the above construction of the image processor, it is not necessary to buffer image pick-up data for one frame, thereby lessening the burden of the image processor. Since the time variation noises are removable in real time, it is effective at the time of dynamic image pick-up, for example.

Preferably, the corrective pixel area is disposed adjacent the main pixel area. Where light or radiation irradiates the entire light or radiation detecting device, the corrective pixel area may be disposed at one end or opposite ends of the radiation detecting device.

This allows the corrective pixel area to be disposed adjacent the main pixel area which is variable with an irradiation area of the light or radiation. Even if the main pixel area is part of the radiation or light detecting device, the time variation noises can be acquired properly by arranging the corrective pixel area immediately next thereto.

Effects of the Invention

According to the light or radiation image pickup apparatus of this invention, the light or radiation image pickup apparatus provided removes time variation noises accurately without being influenced by abnormal output of the detecting elements in the corrective pixel area which are sensitive to light or radiation.

| | [Description of References] |
|---|---|
| 1 | X-ray tube |
| 3 | X-ray detector |
| 4 | A/D converter |
| 5 | image processor |
| 11 | X-ray detection controller |
| 12 | gate drive circuit |
| 13 | amplifier array |
| 14 | sample hold unit |
| 15 | multiplexer |
| 22 | charge-to-voltage converting amplifiers |
| 23 | image memory unit |
| 24 | offset signal removing unit |
| 25 | time variation noise calculating unit |
| 26 | time variation noise removing unit |
| 27 | time variation noise first calculating unit |
| 28 | time variation noise second calculating unit |
| 29 | time variation noise third calculating unit |
| DU | detecting elements |
| S | detecting surface |
| A1 | main pixel area |
| B1 | corrective pixel area |
| GL1-GL10 | gate lines |
| DL1-DL10 | data lines |
| SH1-SH10 | sample hold circuits |

EMBODIMENT

An embodiment of this invention will be described hereinafter with reference to the drawings.

Figure 1:
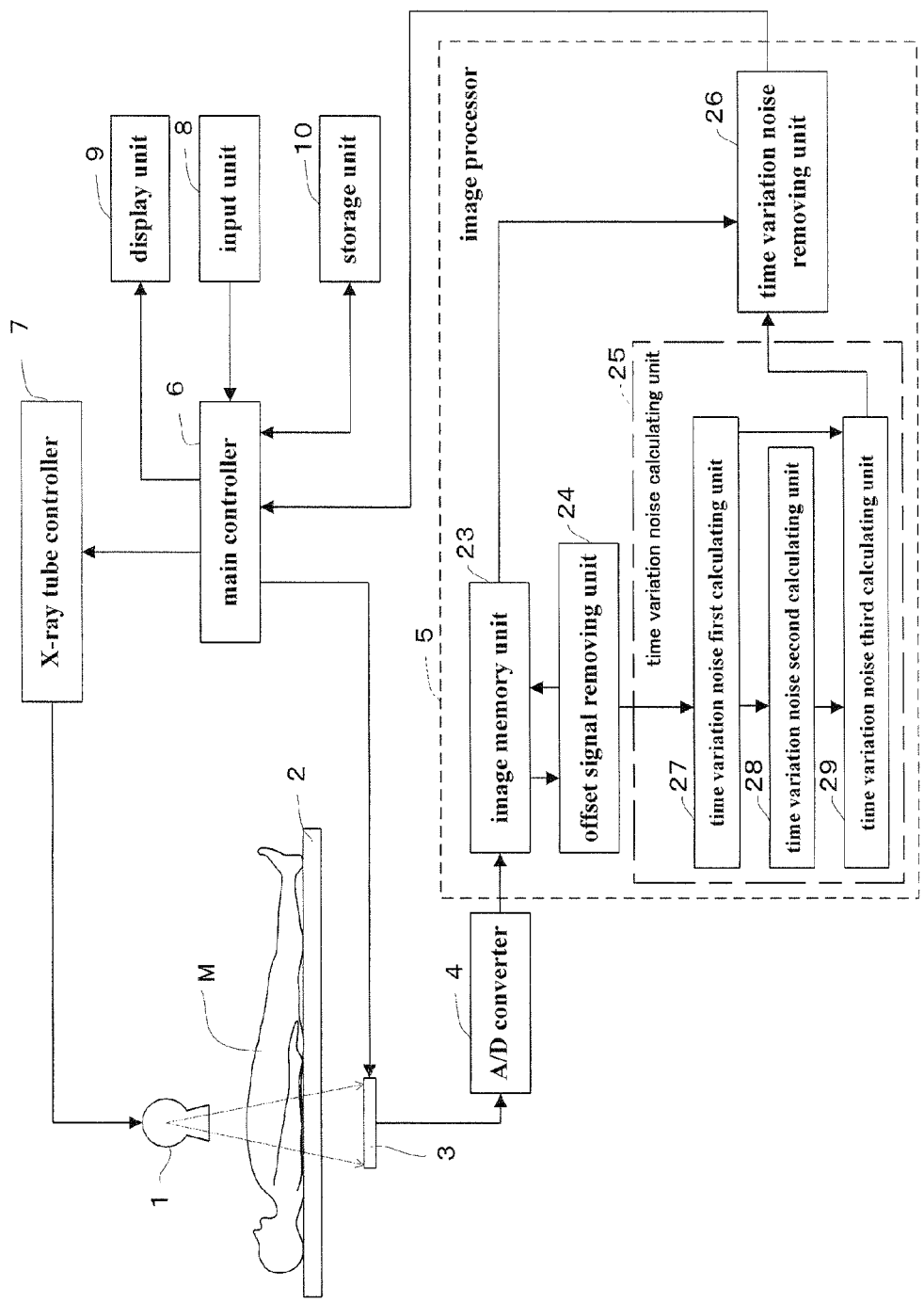
FIG. 1 is a block diagram showing an overall construction of an X-ray image pickup apparatus according to an embodiment.
Figure 2:
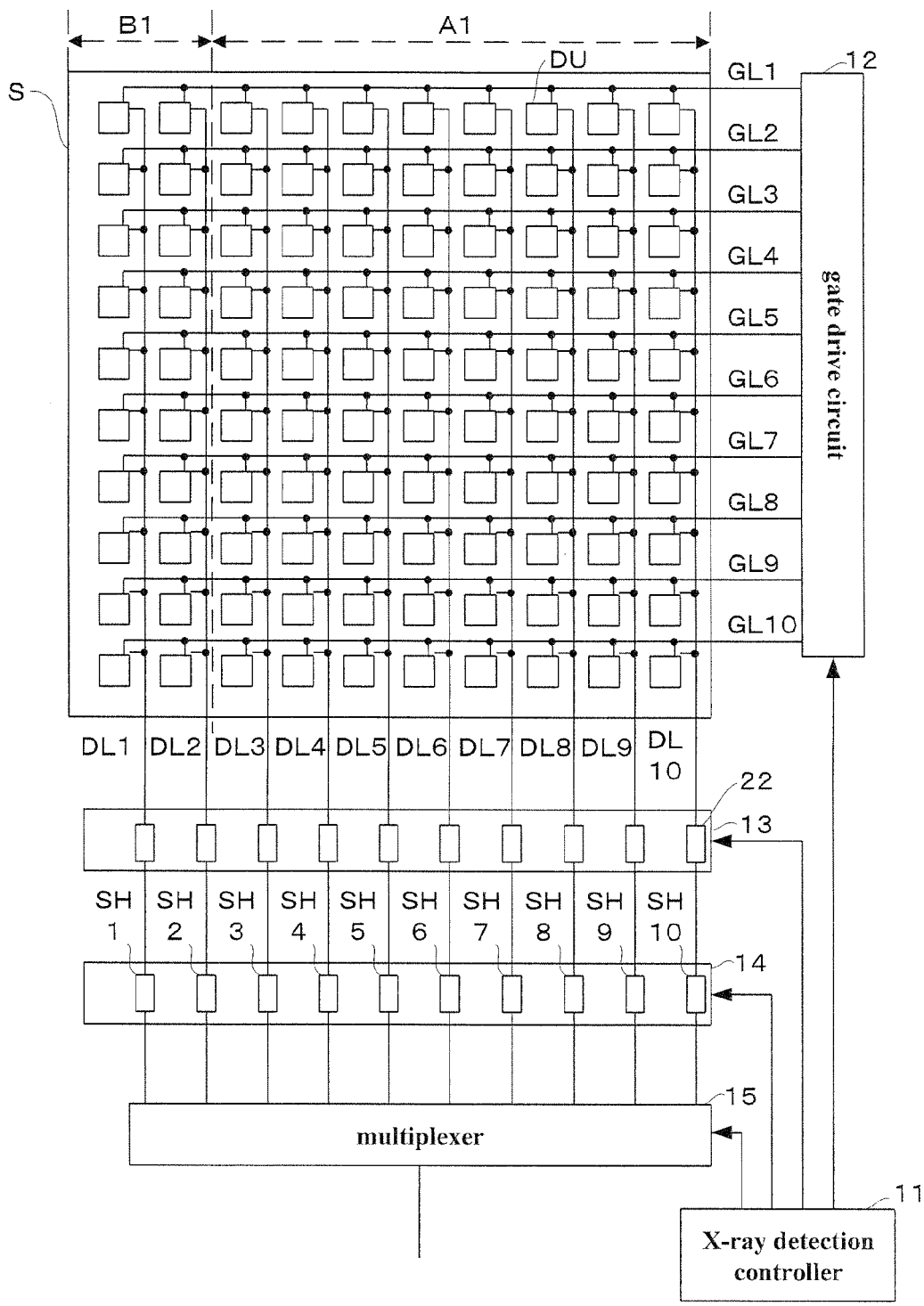
FIG. 2 is a circuit diagram showing a construction of an X-ray detector included in the X-ray image pickup apparatus according to the embodiment.
Figure 3:
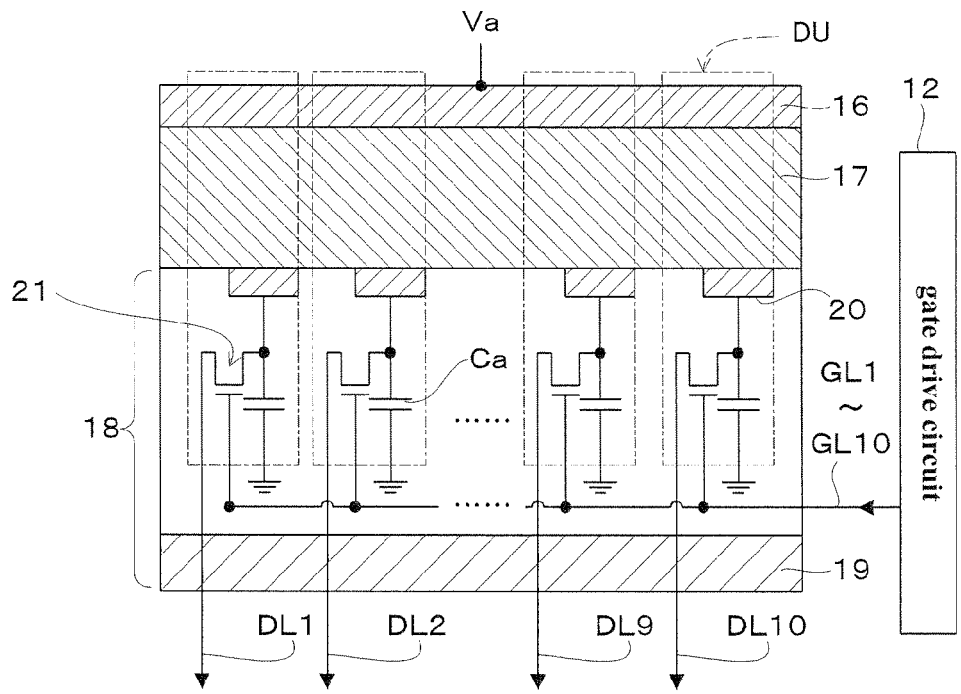
FIG. 3 is a schematic view in vertical section of an X-ray conversion layer and adjacent components of the X-ray detector included in the X-ray image pickup apparatus according to the embodiment.
Figure 4:
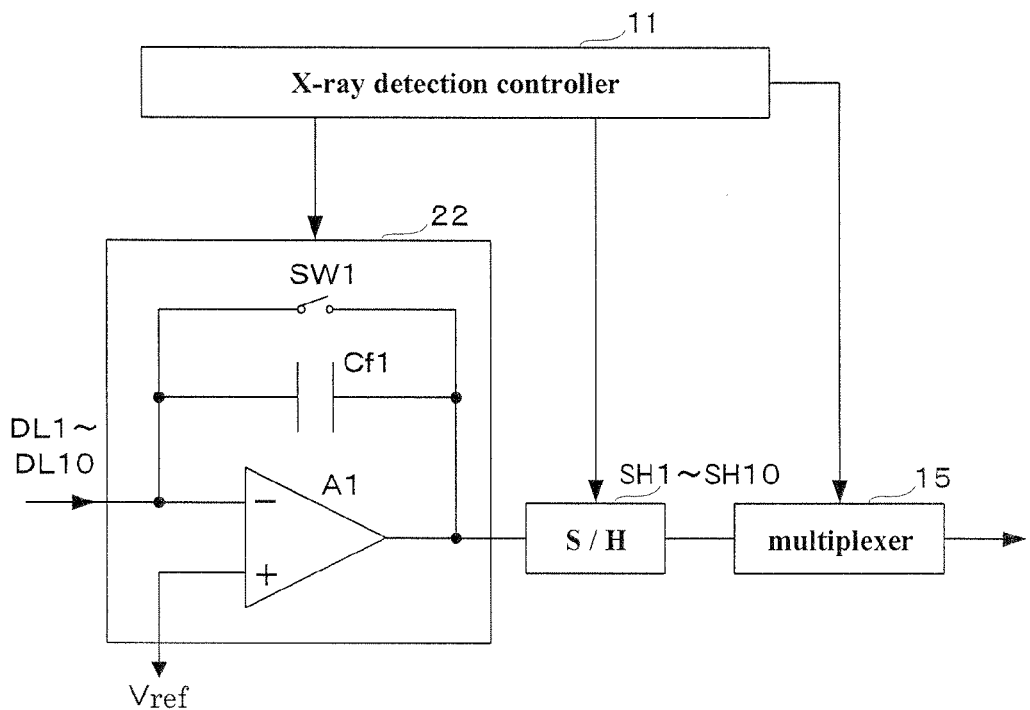
FIG. 4 is a block diagram showing a construction of an amplifier array according to the embodiment.

FIG. 1 is a block diagram showing a construction of an X-ray image pickup apparatus according to the embodiment. FIG. 2 is a circuit diagram showing a construction of an X-ray detector included in the X-ray image pickup apparatus. FIG. 3 is a schematic view in vertical section of an X-ray conversion layer and adjacent components of the X-ray image pickup apparatus. FIG. 4 is a block diagram showing a construction of an amplifier array. In this embodiment, description will be made taking X-rays as an example of incident light or radiation, and description will be made taking an X-ray image pickup apparatus as an example of radiation image pickup apparatus.

<X-Ray Image Pickup Apparatus>

The X-ray image pickup apparatus according to this embodiment picks up images by irradiating a patient with X-rays. Specifically, an X-ray image transmitted through the patient is projected to an X-ray conversion layer (an amorphous selenium film in this embodiment), and is converted into carriers by generating, in the layer, carriers (electric charge signals) proportional to density variations of the image.

As shown in FIG. 1, the X-ray image pickup apparatus includes an X-ray tube 1 for emitting X-rays to a patient M to be imaged, a top board 2 for supporting the patient M, an X-ray planar detector 3 for generating charge signals corresponding to the quantity of X-rays transmitted through the patient M (i.e. detecting X-rays as charge signals) and further converting the charge signals into voltage signals for output, an A/D converter 4 for converting, from analog to digital, the voltage signals outputted from the X-ray planar detector 3, an image processor 5 for processing the digital voltage signals converted by the A/D converter 4 to construct an image, a main controller 6 for carrying out various controls relating to X-ray imaging, an X-ray tube controller 7 for controlling the X-ray tube 1 by generating a tube voltage and a tube current based on the controls by the main controller 6, an input unit 8 capable of inputting settings relating to X-ray image pickup, a display unit 9 for displaying X-ray images processed and produced by the image processor 5 and other information, and a storage unit 10 for storing X-ray images processed and produced by the image processor 5 and other information. Each component of the X-ray image pickup apparatus will be further described in detail.

As shown in FIG. 2, the X-ray planar detector 3 has a plurality of X-ray detecting elements DU, an X-ray detection controller 11, a gate drive circuit 12, an amplifier array 13, a sample hold unit 14 and a multiplexer 15. The plurality of X-ray detecting elements DU are connected to the gate drive circuit 12 by gate lines G1-G10, and are connected to the amplifier array 13 by data lines DL1-DL10. The X-ray detection controller 11 is connected to the gate drive circuit 12, amplifier array 13, sample hold unit 14 and multiplexer 15. The X-ray planar detector 3 corresponds to the light or radiation detecting device in this invention.

The X-ray detecting elements DU output charge signals in response to incident X-rays, and are arranged vertically and horizontally in a two-dimensional matrix form on an X-ray detecting surface S on which X-rays are incident. The X-ray detecting elements DU are arranged in the two-dimensional matrix form, for example, in the order of 4096 columns×4096 rows on the actual X-ray detecting surface S. FIG. 2 shows, as an example, X-ray detecting elements DU arranged in the two-dimensional matrix form of ten columns×ten rows.

The X-ray detecting surface S in the X-ray planar detector 3 is divided into a main pixel area A1 and a corrective pixel area B1. In this embodiment, the corrective pixel area B1 is disposed at the left end of the X-ray detecting surface S. The detecting elements DU arranged in the main pixel area A1 are used for measuring a dose of radiation transmitted through the patient M. The detecting elements DU arranged in the corrective pixel area B1 are used for measuring time variation noises, and about 30-60 of them, for example, are arranged in each row. Two of them are arranged in FIG. 2.

As shown in FIG. 3, the X-ray detecting elements DU have a voltage application electrode 16 for applying a bias voltage Va of high voltage, an X-ray conversion layer 17 for converting incident X-rays into charge signals, and an active matrix substrate 18 for collecting, accumulating, and reading (outputting) the charge signals converted by the X-ray conversion layer 17.

The X-ray conversion layer 17 consists of an X-ray sensitive semiconductor, and is formed of noncrystalline, amorphous selenium (a-Se) film, for example. It is constructed such that, when X-rays impinge on the X-ray conversion layer 17, a predetermined number of carriers (charge signals) proportional to the energy of X-rays are generated directly (direct conversion type).

As shown in FIG. 3, the active matrix substrate 18 has an insulating glass substrate 19, and on this glass substrate 19 are collecting electrodes 20 for collecting the charge signals converted by the X-ray conversion layer 17 based on the bias voltage Va applied from the voltage application electrode 16, capacitors Ca for accumulating the charge signals collected by the collecting electrodes 20, TFTs 21 acting as switching elements, gate lines GL1-GL10 for controlling the TFTs 21 from the gate drive circuit 12, and data lines DL1-DL10 for reading the charge signals from the TFTs 21.

Next, the X-ray detection controller 11 is controlled from the main controller 6 (see FIG. 1), as shown in FIG. 2, to carry out overall control of the gate drive circuit 12, amplifier array 13, sample hold unit 14 and multiplexer 36, and carry out controls to take out successively and selectively the charge signals detected by the X-ray detecting elements DU to the amplifier array 13, and further to output them successively from the multiplexer 15. Specifically, the X-ray detection controller 11 is constructed to output a gate actuating signal for starting operation of the gate drive circuit 12, an amplifier resetting signal for starting amplifier resetting of the amplifier array 13, a sample hold control signal for controlling operation of the sample hold unit 14, and a multiplexer control signal for controlling operation of the multiplexer 15.

Next, the gate drive circuit 12 operates the TFT 21 of each X-ray detecting element DU to take out successively and selectively the charge signals detected by the X-ray detecting elements DU. The gate drive circuit 12, based on the gate actuating signal from the X-ray detection controller 11, successively selects the gate lines GL1-GL10 commonly connected to the respective rows of X-ray detecting elements DU, and transmits a gate signal thereto. The TFTs 21 of X-ray detecting elements DU in a selected row are turned on all at once by the gate signal, to output the charge signals accumulated in the capacitors Ca to the amplifier array 13 through the data lines DL1-DL10. The gate drive circuit 12 corresponds to the reading device in this invention. The gate signal corresponds to the switching signal in this invention.

Next, as shown in FIG. 2, the amplifier array 13 includes charge-to-voltage converting amplifiers 22 corresponding in number (ten in FIG. 2) to the data lines DL1-DL10 provided for the respective columns of X-ray detecting elements DU. The charge-to-voltage converting amplifiers 22 are charge sensitive amplifiers (CSA) for converting the charge signals outputted from the respective X-ray detecting elements DU into voltage signals. After the amplifier resetting signal from the X-ray detection controller 11 stops, the charge-to-voltage converting amplifiers 22 convert the charge signals into the voltage signals for output to the sample hold unit 14. The amplifier array 13 corresponds to the charge-to-voltage converting device in this invention.

Further, an electrical structure of the charge-to-voltage converting amplifier 22 will be described in detail using FIG. 4. As shown in FIG. 4, the charge-to-voltage converting amplifier 22 is an amplifying element having an operational amplifier A1 with an inverting input terminal connected to data line DL1-DL10, a feedback capacitor Cf1 disposed between the inverting input terminal and an output terminal of this operational amplifier A1, and a switch SW1 provided in parallel with this feedback capacitor Cf1. A reference voltage Vref is applied to a non-inverting input terminal of the operational amplifier A1. The reference voltage Vref is at grounding level (0[VD]).

The switch SW1 changes to a conduction state and a cut-off state, based on control from the X-ray detection controller 11. Specifically, the switch SW1 becomes the conduction state at a predetermined time based on the amplifier resetting signal from the X-ray detection controller 11. When the switch SW1 is in the conduction state, electric charges (charge signals) accumulated in the feedback capacitor Cf1 are discharged, the feedback capacitor Cf1 becomes a reset state, and the charge-to-voltage converting amplifier 22 becomes an initialized state. When the switch SW1 assumes the cut-off state after the predetermined time, the initialized state is canceled and, at and after this point of time, the charge signals inputted from the data line DL1-DL10 are accumulated as voltage signals in the feedback capacitor Cf1. Thus, the charge-to-voltage converting amplifier 22 has a construction for outputting voltages according to the charge signals inputted at and after the time of the initialized state is canceled.

Next, the sample hold unit 14 includes sample hold circuits SH1-SH10 corresponding in number to the number of charge-to-voltage converting amplifiers 22. Based on the sample hold control signal from the X-ray detection controller 12, the voltage signals outputted from the charge-to-voltage converting amplifiers 22 are sampled at a predetermined time, the voltage signals are held upon elapse of the predetermined time, and voltage signals in a stable state are outputted to the multiplexer 15. The sample hold unit 14 corresponds to the voltage signal holding device in this invention.

Next, the multiplexer 15 has, mounted inside, switches corresponding in number to the number of sample hold circuits SH1-SH10. Based on the multiplexer control signal from the X-ray detection controller 12, the switches are switched to ON state one after another, to output to the AM converter 4 shown in FIG. 1 a time sharing signal which bundles each of the voltage signals outputted from the sample hold circuits SH1-SH10.

Next, the A/D converter 4 samples each voltage signal in the time sharing signal from the multiplexer 15 with predetermined timing, converts it into each voltage signal of a digital time sharing signal, and outputs it to the image processor 5.

As shown in FIG. 1, the image processor 5 has, in its interior, an image memory unit 23, an offset signal removing unit 24, a time variation noise calculating unit 25 and a time variation noise removing unit 26. Further, the time variation noise calculating unit 25 includes a time variation noise first calculating unit 27, a time variation noise second calculating unit 28 and a time variation noise third calculating unit 29.

The voltage signals in the digital time sharing signals outputted from the A/D converter 4 are temporarily stored in the image memory unit 23. Offset signals measured beforehand are also stored in the image memory unit 23. Here, the offset signals can be acquired by averaging a plurality of dark images picked up when X-rays are not emitted from the X-ray tube 1. Of course, time variation noises are included also in the dark images, but the time variation noises are offset by averaging the plurality of image signals, thereby imparting hardly any influence on the offset signals.

The offset signal removing unit 24 removes the offset signals from the voltage signals outputted from the A/D converter 4. If the voltage signals outputted from the A/D converter 4 are main pixel detection signals from the detecting elements DU in the main pixel area A1, they are stored in the image memory unit 23 again. Corrective voltage signals from the detecting elements DU in the corrective pixel area B1 are outputted to the time variation noise calculating unit 25. Here, in this embodiment, the voltage signals inputted from the detecting pixels DU in the main pixel area A1 through the data lines DL3-D10, amplifier array 13, sample hold unit 14 and multiplexer 15 to the image processor 5 are called the main pixel detection signals. The voltage signals inputted from the detecting pixels DU in the corrective pixel area B1 through the data line DL1 or D2, amplifier array 13, sample hold unit 14 and multiplexer 15 to the image processor 5 are called the corrective voltage signals.

The time variation noise calculating unit 25 calculates a time variation noise for each gate line, and outputs it to the time variation noise removing unit 26. A method of calculating this time variation noise will be described in detail later.

The time variation noise removing unit 26 removes the time variation noises outputted from the time variation noise calculating unit 25, from the main pixel detection signals stored in the image memory unit 23, thereby to constructs a radiological image without noise.

<X-Ray Image Pickup>

Next, operation of the X-ray image pickup apparatus in this embodiment to carry out X-ray image pickup will be described using FIGS. 1-9.

First, as shown in FIGS. 1-3, when an X-ray image pickup start is instructed through the input unit 8, the main controller 6 controls the X-ray tube controller 7 and the X-ray detection controller 11 of X-ray planar detector 3. The X-ray tube controller 7 generates a tube voltage and a tube current based on the control from the main controller 6, and controls the X-ray tube 1 whereby X-rays are emitted from the X-ray tube 1 to the patient M. The X-rays transmitted through the patient M are converted into charge signals corresponding to an X-ray dosage transmitted through the patient M by the X-ray detecting elements DU of X-ray planar detector 3, to be stored in the capacitors Ca.

Figure 5:
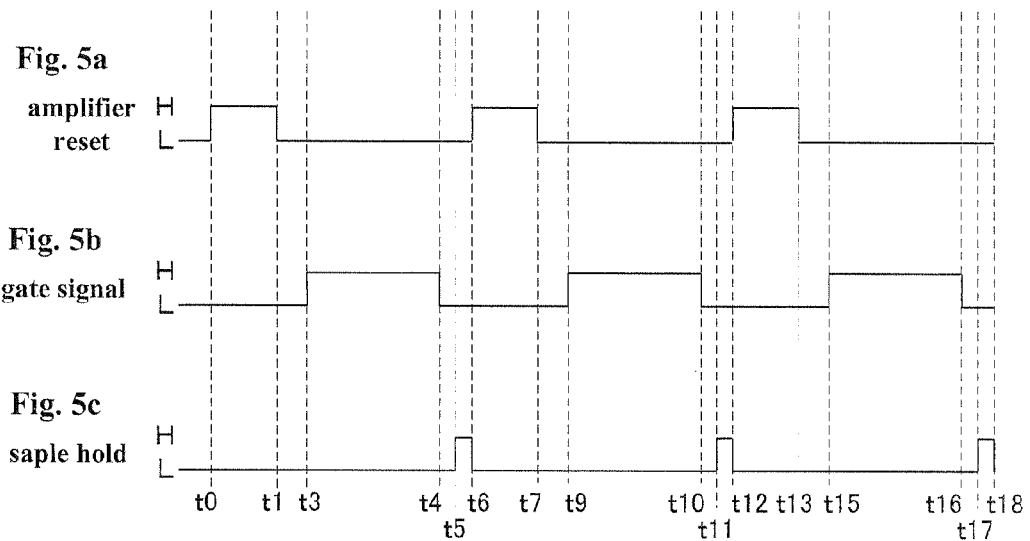
FIG. 5 is a timing chart of an X-ray detection controller for pixels in a main pixel area according to the embodiment.

Next, operation of the gate drive circuit 12 connected through the gate lines GL1-GL10 to the respective detecting elements DU arranged in the main pixel area A1, operation of the amplifier array 13 and sample hold unit 14 connected through the data lines DL3-DL10, and operation of the X-ray detection controller 11 which controls these, will be described using FIG. 5. The X-ray detection controller 11 outputs an amplifier resetting signal to the charge-to-voltage converting amplifiers 22 of the amplifier array 13 based on the control from the main controller 6. In response to the amplifier resetting signal, the switches SW1 of the charge-to-voltage converting amplifiers 22 become conductive in ON state, to reset the feedback capacitors Cf1. As shown in FIG. 5 (a), the charge-to-voltage converting amplifiers 22 are initialized (t0-t1). After the initialization of the charge-to-voltage converting amplifiers 22 is finished, the X-ray detection controller 11 outputs a gate actuating signal to the gate drive circuit 12. In response to this gate actuating signal, as shown in FIG. 5 (b), the gate drive circuit 12 successively selects the gate lines (t3-t4). This embodiment will be described, assuming that gate lines G1, G2, G3, . . . , G9 and G10 are selected in order, one at a time. The X-ray detection controller 11 corresponds to the control device in this invention.

First, the gate drive circuit 12 selects the gate line G1 to designate each detecting element DU connected to the gate line G1. Voltage is applied by the transmitted gate signal to the gate of TFT 21 of each designated detecting element DU to be in ON state. Consequently, the carriers stored in the capacitors Ca connected to the TFTs 21 designated are read to the data lines DL3-DL10 via TFTs 21. Next, the gate drive circuit 12 selects the gate line G2 to designate each detecting element DU connected to the gate line G2, and through the same procedure, the charge signals stored in the capacitors Ca of the designated detecting elements DU are read in the order of data lines D3-D10. The remaining gate lines G3-G10 are selected similarly in order, to read the carriers in two dimensions.

Thus, the gate drive circuit 12 successively selects the gate lines GL1-GL10 to designate the detecting elements DU connected to each gate line. The charge signals stored in the capacitors Ca of the designated detecting elements DU are read to the data lines DL3-DL10.

The charge signals read to each data line are amplified while being converted into voltage signals by the charge-to-voltage converting amplifier 22 to be accumulated in the feedback capacitor Cf1.

And the X-ray detection controller 11, after stopping the gate actuating signal to the gate drive circuit 12, sends a sample hold control signal to the sample hold circuits SH3-SH10 connected to the data lines D3-D10 through the amplifier array 13. In response to this signal, the sample hold circuits SH3-SH10, as shown in FIG. 5 (c), sample and once hold the voltage signals converted in the amplifier array 13 (t5-t6).

Subsequently, the X-ray detection controller 11 sends a multiplexer control signal to the multiplexer 15. In response to this signal, the voltage signals held by the sample hold circuits SH3-SH10 are outputted successively from the multiplexer 15 as time sharing signals. The outputted voltage signals are converted from analog values into digital values by the A/D converter 4. Based on these converted digital signals, the image processor 5 carries out signal processing and constructs a two-dimensional pickup image.

Figure 6:
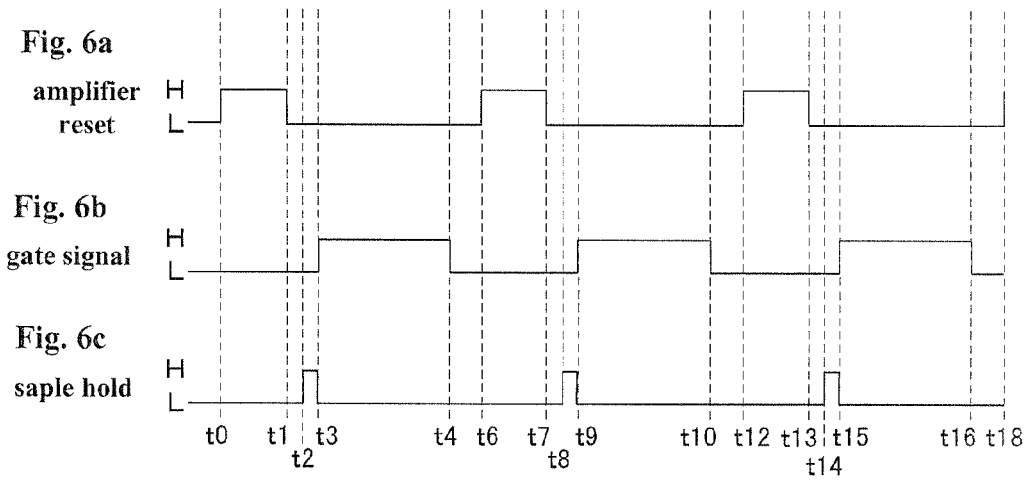
FIG. 6 is a timing chart of the X-ray detection controller for pixels in a corrective pixel area according to the embodiment.

Next, operation of the gate drive circuit 12 connected through the gate lines GL1-GL10 to the respective detecting elements DU arranged in the corrective pixel area B1, operation of the amplifier array 13 and sample hold unit 14 connected through the data line DL1 or DL2, and operation of the X-ray detection controller 11 which controls these, will be described using FIG. 6.

The X-ray detection controller 11 outputs an amplifier resetting signal to the charge-to-voltage converting amplifiers 22 of the amplifier array 13 based on the control from the main controller 6. In response to the amplifier resetting signal, as shown in FIG. 6 (a), the charge-to-voltage converting amplifiers 22 are initialized (t0-t1). After the initialization of the charge-to-voltage converting amplifiers 22 is finished, the X-ray detection controller 11 outputs a sample hold control signal to the sample hold circuits SH1 and SH2. In response to this signal, the sample hold circuits SH1 and SH2, as shown in FIG. 6 (c), sample and once hold the voltage signals accumulated in capacitors Cf1 of the charge-to-voltage converting amplifiers 22 (t2-t3).

That is, the timing of sampling and holding for the detecting elements DU arranged in the corrective pixel area B1 and the timing of sampling and holding for the detecting elements DU arranged in the main pixel area A1 are staggered to times before and after the gate signal is sent from the gate drive circuit 12. For the detecting elements DU arranged in the main pixel area A1, after sending the gating signal to the detecting elements DU, the charge signals in the detecting elements DU are read to the amplifier array 13 and converted into voltage signals, and these voltage signals are sampled and held.

On the other hand, for the detecting elements DU arranged in the corrective pixel area B1, before sending the gating signal to the detecting elements DU, that is before reading the charge signals in the detecting elements DU to the amplifier array 13, the voltage signals which are voltage signals already converted from the charge signals in the amplifier array 13 are sampled and held. In this case, since it is before the gating signal is sent to the detecting elements DU, the TFTs 21 of the detecting elements DU are in OFF state, and the charge signals stored in the capacitors Ca cannot be read into the amplifier array 13. That is, the voltage signals sampled and held by the sample hold circuits SH1 and SH2 are voltage signals with time variation noises generated in the path from the gates of TFTs 21 of the detecting elements DU arranged in the corrective pixel area B1 through the data line DL1 or DL2 to the charge-to-voltage converting amplifier 22, and accumulated in the capacitor Cf1 of the charge-to-voltage converting amplifier 22, after the charge-to-voltage converting amplifier 22 is reset. These voltage signals include also time variation noises generated in the data line DL1 or DL2 and the charge-to-voltage converting amplifier 22.

Subsequently, the X-ray detection controller 11 outputs the gate actuating signal to the gate drive circuit 12 as already described above. In response to this gate actuating signal, as shown in FIG. 6 (b), the gate drive circuit 12 selects the gate lines successively (t3-t4). In this way, as in the case of the detecting elements DU belonging to the main pixel area A1, the charge signals stored in the capacitors Ca of the detecting elements DU belonging to the corrective pixel area B1 are read and accumulated in the capacitors Cf1 in the charge-to-voltage converting amplifiers 22. Since sampling has already been carried out, the voltage signals converted from the charge signals generated by the detecting elements DU and accumulated in the capacitors Ca are erased at the time of amplifier resetting, without being sent to the image processor.

Subsequently, the X-ray detection controller 11 sends a multiplexer control signal to the multiplexer 15. In response to this signal, the voltage signals held by the sample hold circuits SH1-SH2 are outputted successively from the multiplexer 15 as time sharing signals. The outputted voltage signals are converted from analog values into digital values by the A/D converter 4. These digital signals converted to digital values are sent to the image processor 5 to be put to image processing.

<Time Variation Noise Removal>

Next, a method of removing the time variation noises from the main pixel detection signals detected by the detecting pixels DU in the main pixel area A1 will be described.

The main pixel detection signals acquired from the paths extending from the detecting elements DU in the main pixel area A1 to the image processor 5 are formed of three signal components, as follows:

(main pixel detection signals)=(X-ray transmission image signals)+(time variation noise signals)+(offset signals).

Now, by removing the offset signals measured beforehand, voltage signals consisting of (X-ray transmission image signals)+(time variation noise signals)

are obtained.

On the other hand, the corrective voltage signals acquired from the paths extending from the detecting pixels DU in the corrective pixel area B1 to the image processor 5 are formed of two components, as follows:

(corrective voltage signals)=(time variation noise signals)+(offset signals).

Thus, the image processor 5 obtains the (time variation noise signals) by removing the offset signals measured beforehand.

X-ray transmission image signals free from noise can be obtained by removing the time variation noise signals included in the corrective voltage signals acquired from the corrective pixel area B1, from the main pixel detection signals acquired from the detecting elements DU in the main pixel area A1. There are some methods as methods of calculating the time variation noises, and these will be described.

Figure 7:
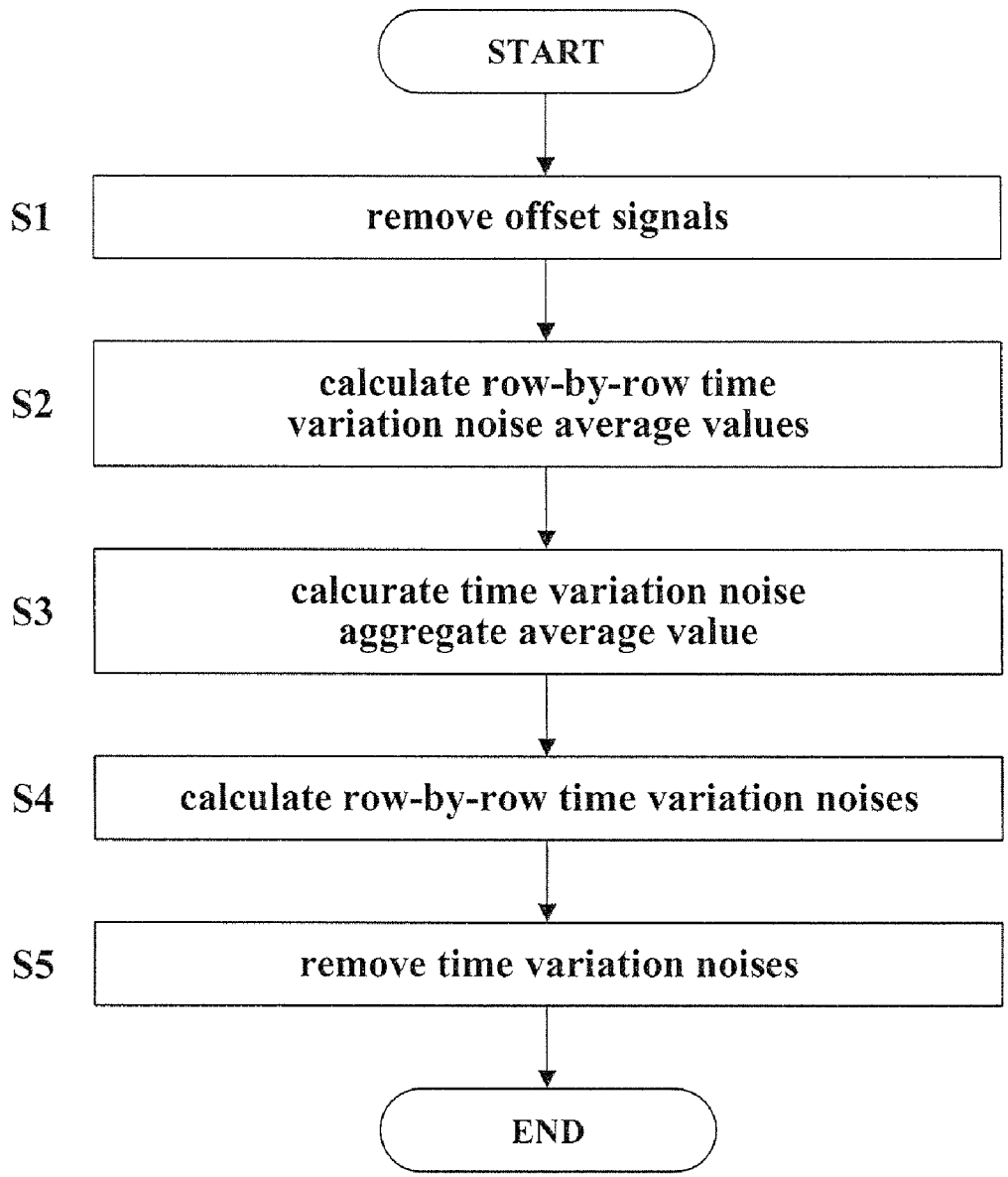
FIG. 7 is a flow chart showing a sequence of removing time variation noises according to the embodiment.
Figure 8:
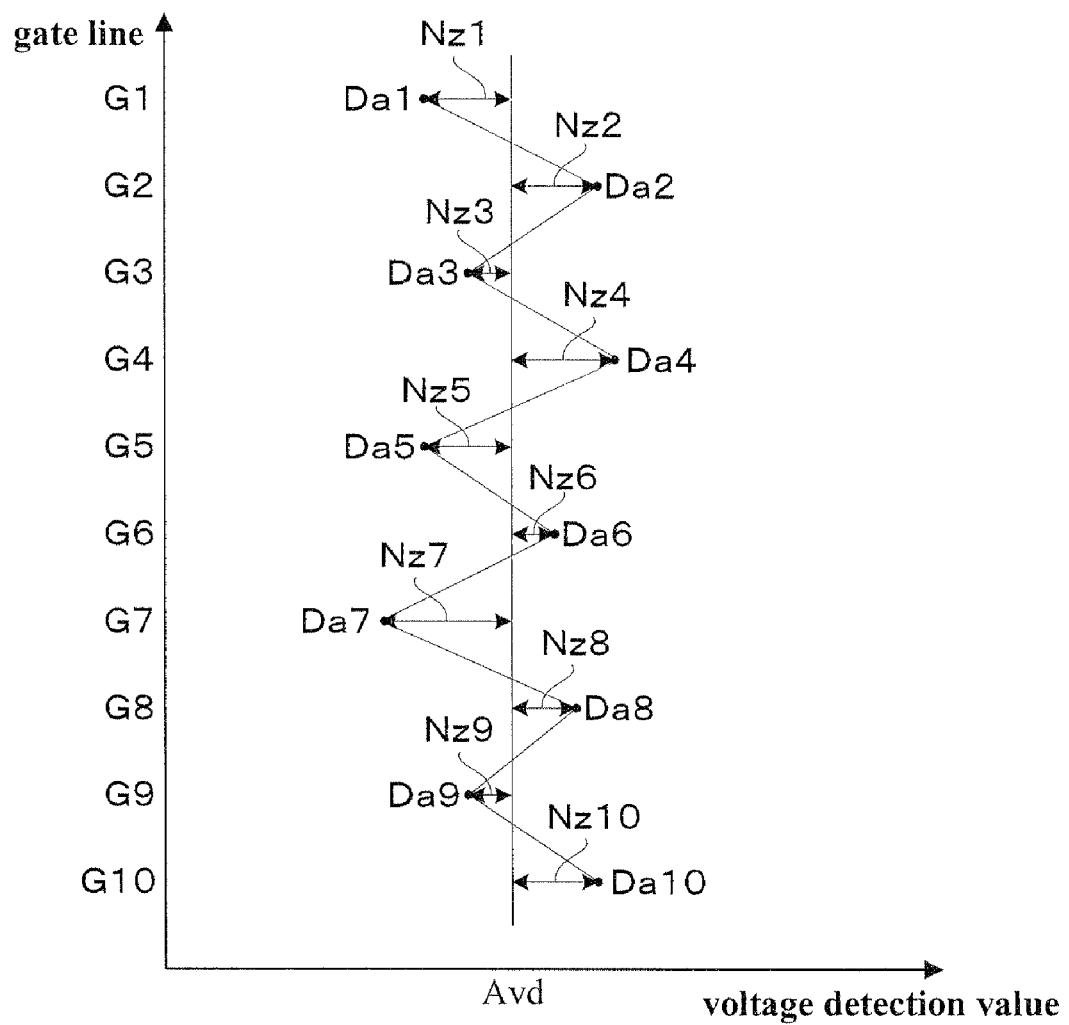
FIG. 8 is an explanatory view showing calculation of the time variation noises according to the embodiment.

A method of removing the time variation noises by additive average will be described with reference to FIGS. 1 and 7.

The image processor 5 removes the time variation noise signals from the main pixel detection signals with a method described below, using the main pixel detection signals acquired from the paths extending from the main pixel area A1 and the corrective voltage signals acquired from the paths extending from the corrective pixel area B1 by the method described above. First, a method of removing the time variation noises in a still image will be described.

(Step 1) Remove Offset Signals

The offset signal removing unit 24 removes the offset signals by subtracting the offset signals measured beforehand for the respective detecting elements DU from the main pixel detection signals and the corrective voltage signals stored in the image memory unit 23. The main pixel detection signals from which the offset signals have been removed are stored in the memory unit 37 again. The corrective voltage signals from which the offset signals have been removed are sent to the time variation noise calculating unit 25.

(Step 2) Calculate Row-By-Row Time Variation Noise Average Values

Next, the time variation noise first calculating unit calculates an average value for each gate line of the corrective voltage signals with the offset signals removed therefrom in step 1, to obtain row-by-row time variation noise average values. Since there are ten gate lines in this embodiment, a row-by-row time variation noise average value is calculated for each of the gate lines GL1-GL10, to obtain ten row-by-row time variation noise average values Da1-Da10. The time variation noise average values Da1-Da10 are sent to the time variation noise second calculating unit and time variation noise third calculating unit.

(Step 3) Calculate Time Variation Noise Aggregate Average Value

Next, the time variation noise second calculating unit calculates an average of the time variation noise average values Da1-Da10 calculated in step 2. That is, a time variation noise aggregate average value Avd is calculated, which is an average value of all the corrective voltage signals obtained from all the detecting elements DU in the corrective pixel area B1, with the offset signals removed therefrom. And the time variation noise aggregate average value Avd is sent to the time variation noise third calculating unit.

(Step 4) Calculate Row-By-Row Time Variation Noises

Next, the time variation noise third calculating unit obtains differences, for the respective rows, between the time variation noise aggregate average value Avd and the row-by-row time variation noise average values Da1-Da10. The differences are regarded as row-by-row time variation noises Nz1-Nz10 of the gate lines G1-G10.

(Step 5) Correct Main Pixel Detection Signals

From the main pixel detection signals of the gate lines G1-G10, the corresponding time variation noises Nz1-Nz10 obtained in step 4 are subtracted. Consequently, the X-ray transmission image signals detected by the detecting pixels DU in the main pixel area A1 can be measured accurately. Based on these X-ray transmission image signals, the image processor 5 constructs an X-ray transmission image, and sends the X-ray transmission image to the main controller 6.

According to the above method of calculating time variation noises, the time variation noises for the respective gate lines can be removed from the corresponding main pixel detection signals, and therefore the time variation noises corresponding to the respective gate lines can be removed. The time variation noises can be determined with increased accuracy by subtracting the row-by-row time variation noise average values Da1-Da10 from the time variation noise aggregate average value Avd to obtain row-by-row time variation noises Nz1-Nz10. This method calculates the time variation noise aggregate average value Avd, and therefore is effective when ample time is allowed for carrying out image processing particularly in the case of a still image, for example.

When image processing of a dynamic image is carried out with the above method, an image corrected as described above, even if this is a dynamic image, can be displayed on the monitor provided that the image memory unit 23 holds image data for one image or that a buffer unit for holding image data for one image is included in the image processor 5. Then, even for a dynamic image, an average of all row-by-row time variation noises may be obtained to calculate a time variation noise aggregate average value. At a time of display on the monitor, the frames are displayed with a delay of one frame each.

When image processing is carried out in real time, a moving average method may be used to calculate time variation noises from row-by-row time variation noise average values of three gate lines immediately preceding a gate line of corrective voltage signals for which time variation noises are to be calculated. In this case, the time variation noise second calculating unit averages row-by-row time variation noise average values for the past three rows and a row-by-row time variation noise average value for a row newly processed, thereby to obtain a time variation noise block average value Avbd for the four rows. Row-by-row time variation noises which are differences between this time variation noise block average value Avbd and the row-by-row time variation noise average values may be obtained, and the row-by-row time variation noises may be subtracted from the main pixel detection signals, to display X-ray transmission image signals.

In the embodiment, when deriving time variation noises from the corrective pixel area B1 of detecting elements DU connected to gate line GL6, for example, a time variation noise block average value Avbd of row-by-row time variation noise average values Da3-Da5 of gate lines GL3-GL5 and a row-by-row time variation noise average value Da6 of gate line GL6 is obtained and updated. A row-by-row time variation noise Nz6 is obtained by subtracting the row-by-row time variation noise average value Da6 from the time variation noise block average value Avbd, and is subtracted from the image data from the pixels DU of gate line 6. This may be repeated successively for the subsequently rows.

When there is no immediately preceding row, such as when determining time variation noises from the corrective pixel area B1 of gate line GL1, a time variation noise block average value Avbd of row-by-row time variation noise average values Da7-Da10 of gate lines GL7-GL10, which is calculated for an immediately preceding frame, and a row-by-row time variation noise average value Da1 of gate line GL1 may be obtained and updated. A row-by-row time variation noise Nz1 may be obtained by subtracting the row-by-row time variation noise average value Da1 from the time variation noise block average value Avbd, and may be subtracted from the image data from the pixels DU of gate line 1.

Calculation may always be made from the row-by-row time variation noise average values of the three immediately preceding rows, and calculated time variation noise block average values Avbd may be updated one after another. In this case, row-by-row time variation noises may be obtained by adopting an average value of a time variation noise block average value calculated for one preceding row and a row-by-row time variation noise average value of a current row, as a new time variation noise block average value Avbd.

In this way, the time variation noises can be removed without delaying frames even when picking up a dynamic image. Thus, a pickup image, though it is a real-time fluoroscopic image, can be displayed with the time variation noises removed therefrom. Although the time variation noise block average value Avbd is calculated from the row-by-row time variation noise average values for four rows, an optimal number of rows may be set as appropriate, instead of being limited to four rows.

The X-ray image pickup apparatus 1 constructed as described above can accurately detect and remove time variation noises without being influenced by abnormal output of the detecting elements in the corrective pixel area, such as abnormal output of TFTs 21 or abnormal output due to a deficit of the X-ray conversion layer 17, for example. Since the timing of sampling and holding the corrective voltage signals is before gate driving, charges generated by scattered X-rays are never involved.

Figure 9:
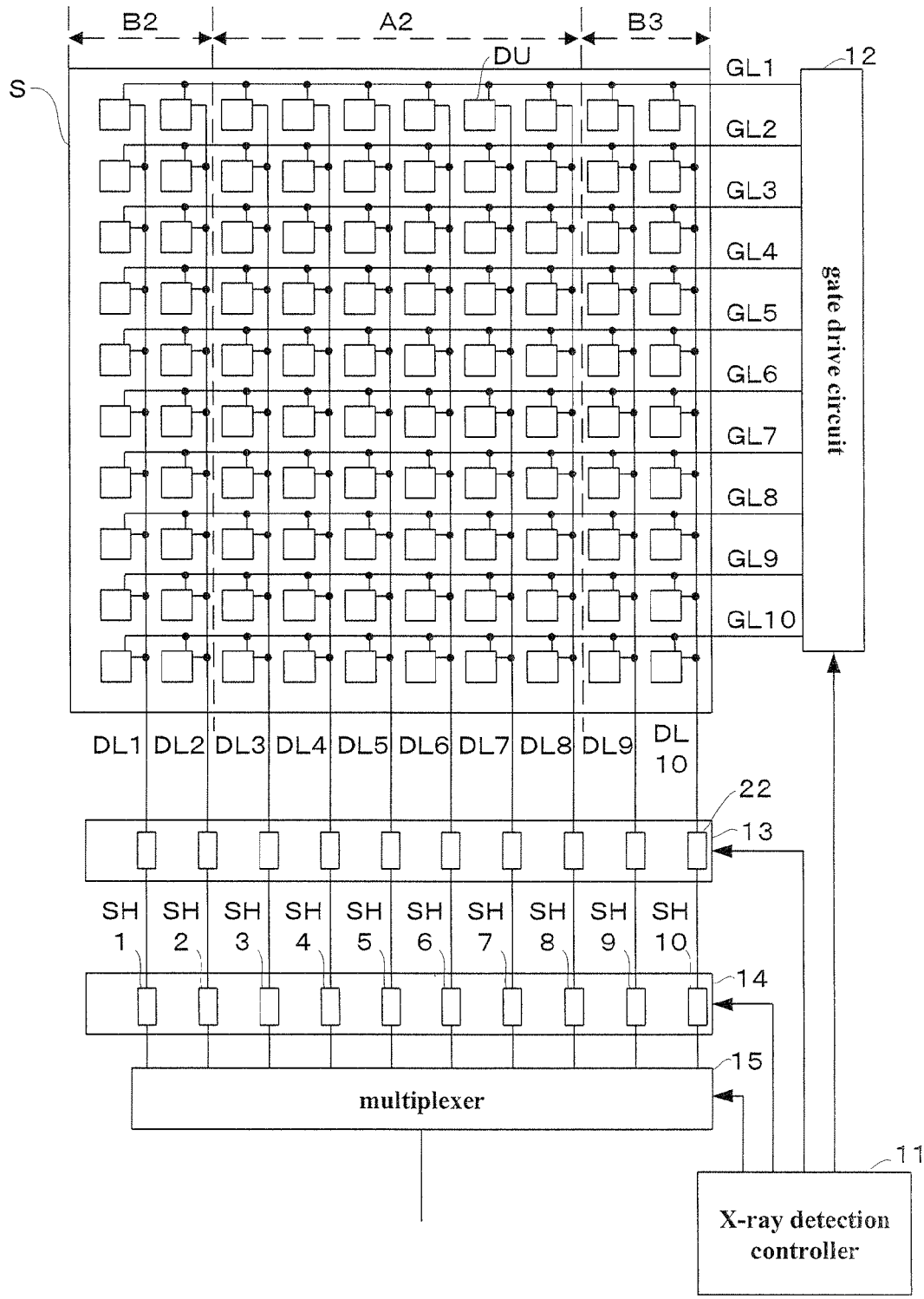
FIG. 9 is a circuit diagram showing a construction of a radiation detector according to another embodiment of this invention.
Figure 10:
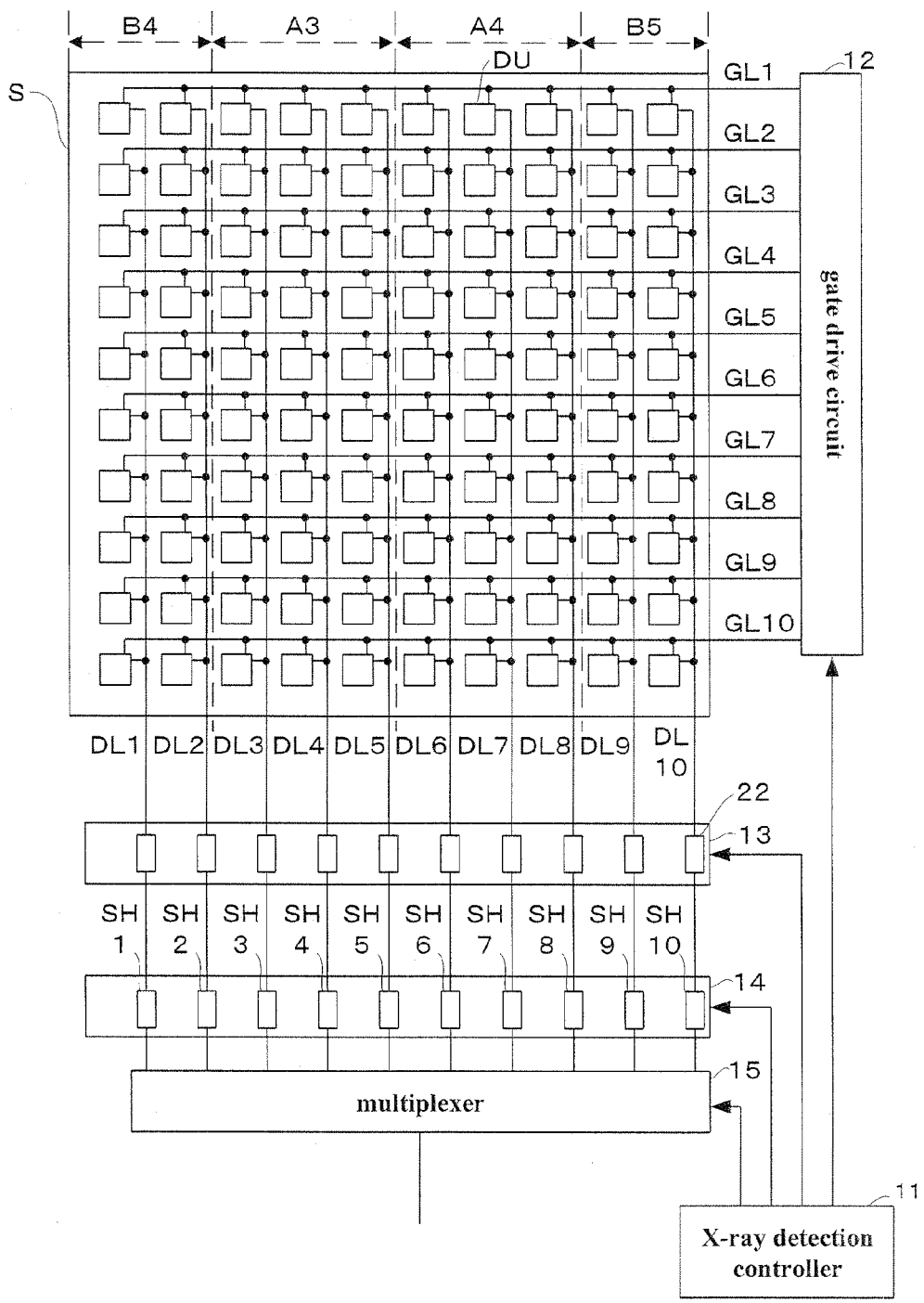
FIG. 10 is a circuit diagram showing a construction of a radiation detector according to another embodiment of this invention.

This invention is not limited to the foregoing embodiment, but may be modified as follows:

(1) In the foregoing embodiment, the corrective pixel area B1 is disposed only at one end of the detecting surface S. Instead, as shown in FIG. 9, a corrective pixel area B2 and a corrective pixel area B3 may be arranged at opposite ends of the detecting surface S. Where the corrective pixel areas are provided at the opposite ends of the detecting surface S, average values of corrective voltage signals of the pixel areas B2 and B3 at the opposite ends may be used. As shown in FIG. 10, the main image area may be divided into two, with correction made independently for main image areas A3 and A4, respectively.

Figure 11:
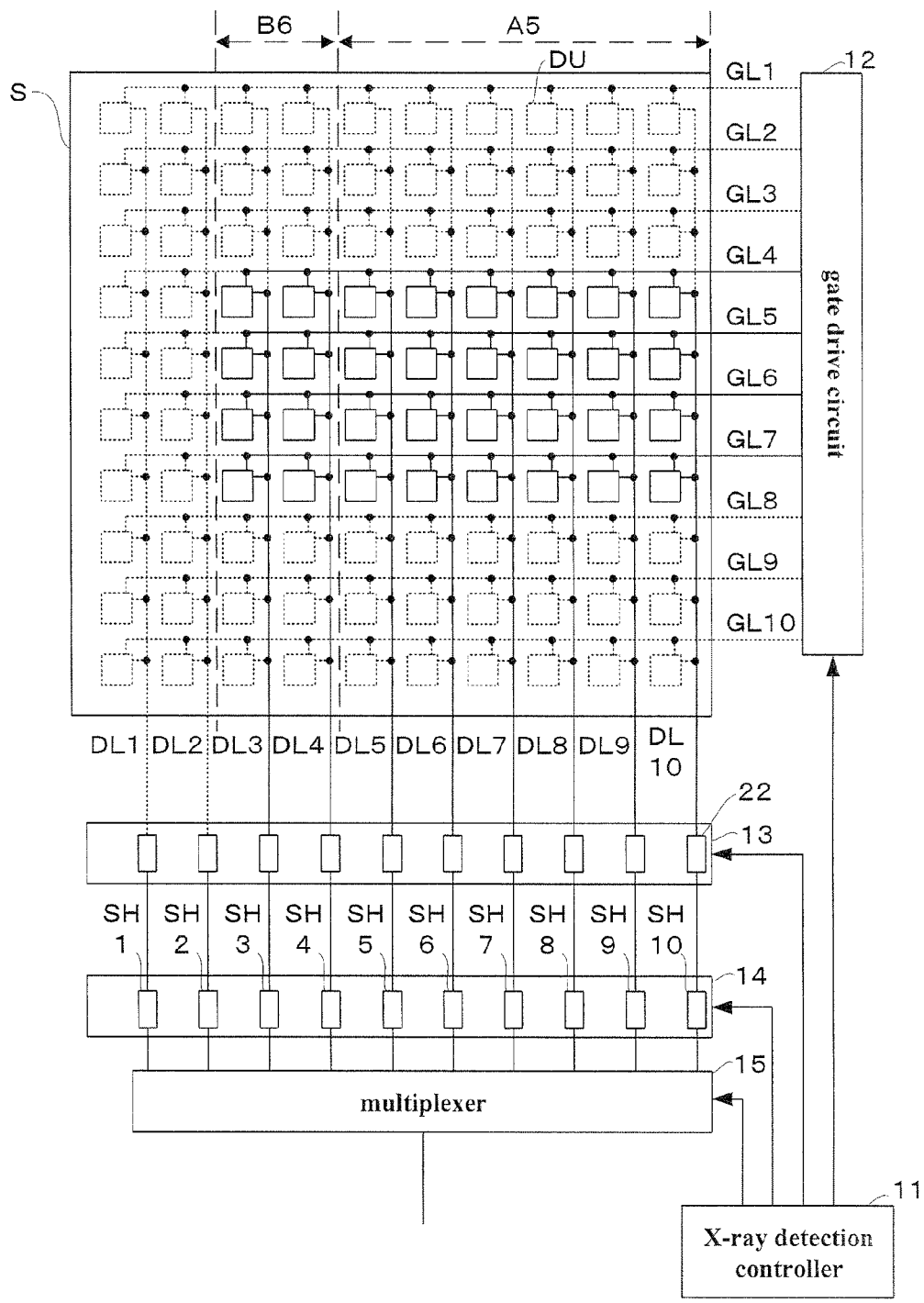
FIG. 11 is a circuit diagram showing a construction of a radiation detector according to another embodiment of this invention.

(2) In the foregoing embodiment, the main pixel area A1 and corrective pixel area B1 are fixed areas. As shown in FIG. 11, when the area of a pickup image is small such as a time of spot radiography, corrective voltage signals may be detected by using a detection area immediately outside a pickup image area A5 as corrective pixel area B6. That is, the detecting elements of the main pixel area can be used as detecting elements of the corrective pixel area. According to this invention, neither the main pixel area nor the corrective pixel area is a fixed area, but can be used for either purpose only by changing the timing of sampling anc. holding for the detecting elements DU.

Figure 12:
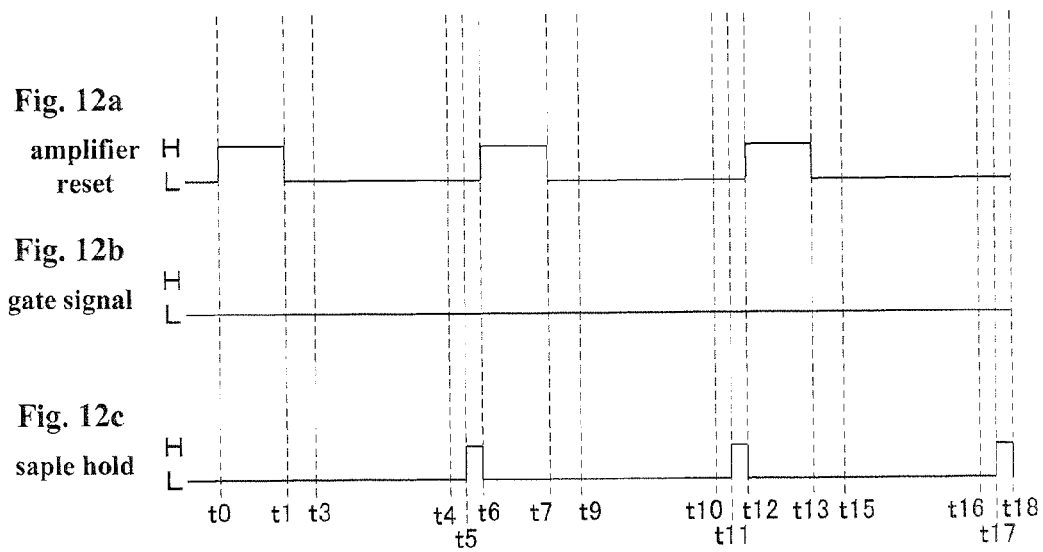
FIG. 12 is a timing chart of an X-ray detection controller for pixels in a corrective pixel area according to another embodiment of this invention.

(3) In the foregoing embodiment, the gate signal is sent also to the TFT circuits of the detecting elements DU of the corrective pixel area B1. Instead, as shown in FIG. 12, a construction for not sending the gate signal to the detecting elements DU of the corrective pixel area B1 may be used. According to this construction, the timing of sampling and holding may be at any time between t1 and t6. Consequently, the corrective voltage signals can be detected since the charges generated in the X-ray conversion layer 17 are not subjected to sampling and holding action.

Figure 13:
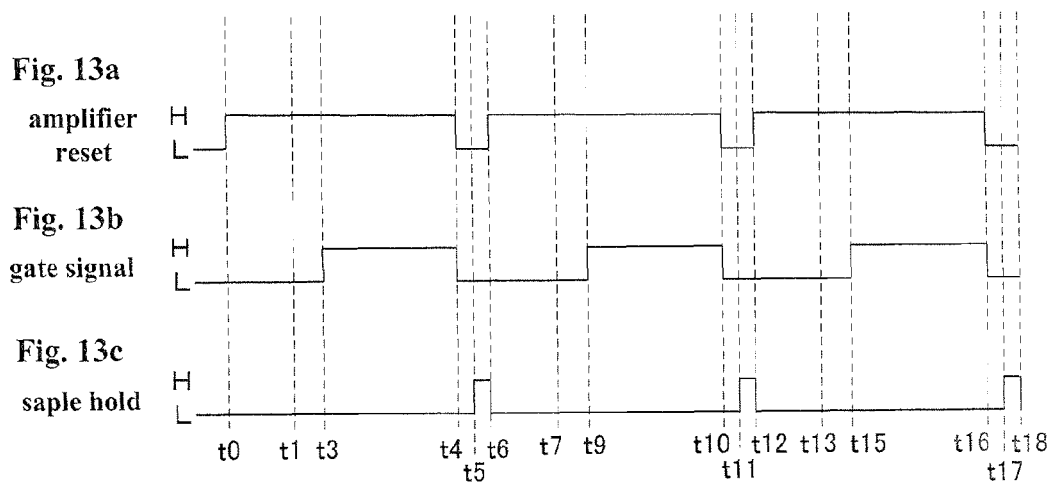
FIG. 13 is a timing chart of an X-ray detection controller for pixels in a corrective pixel area according to another embodiment of this invention.

(4) In the foregoing embodiment, the gates are set to ON after cancellation of resetting of the amplifier array 13 connected to the detecting elements DU of the corrective pixel area B1. As shown in FIG. 13, the amplifier may be reset while the gates are ON. In this construction also, the corrective voltage signals can be detected since the charges generated in the X-ray conversion layer 17 are not subjected to sampling and holding action.

(5) In the foregoing embodiment, the detecting elements DU are X-ray sensitive semiconductors operable in response to X-rays. Employing light sensitive semiconductors will enable manufacture of a light image pickup apparatus which can remove time variation noises with the same construction.

The invention claimed is:

1. A light or radiation image pickup apparatus comprising:
   a light or radiation detecting device having, arranged in a two-dimensional matrix form, a plurality of detecting elements for generating charge signals in response to light or radiation;
   a reading device for sending a switching signal to each row of the two-dimensional matrix of the light or radiation detection device for reading the charge signals;
   a charge-to-voltage converting device for converting the charge signals read from the light or radiation detection device on a row-by-row basis, into voltage signals on a column-by-column basis, respectively;
   a voltage signal holding device for sampling for a given time and holding for a predetermined time, on the column-by-column basis, the voltage signals converted by the charge-to-voltage converting device;
   an image processor for constructing a pickup image from the voltage signals held for the predetermined time by the voltage signal holding device;
   the detecting elements being divided into those arranged in a main pixel area and those arranged in a corrective pixel area within the light or radiation detection device; and
   a control device for performing controls to acquire corrective voltage signals by causing the voltage holding device to sample through the charge-to-voltage converting device, before the switching signal is sent, charge signals generated as different from those generated in response to the light or radiation, in a path extending from the detecting elements arranged in the corrective pixel area to the charge-to-voltage converting device, and to acquire main pixel detection signals by causing the voltage holding device to sample through the charge-to-voltage converting device, after the switching signal is sent, charge signals generated in the main pixel area;
   wherein the image processor forms a pickup image with time variation noises removed therefrom, using the main pixel detection signals and the corrective voltage signals.

2. The light or radiation image pickup apparatus according to claim 1, wherein the image processor includes:
   an offset signal removing unit for removing offset signals from the main pixel detection signals and the corrective voltage signals;
   a time variation noise first calculating unit for calculating row-by-row time variation noise average values which are average values for respective rows of the corrective signals with the offset signals removed therefrom;
   a time variation noise second calculating unit for calculating a time variation noise aggregate average value which is an average value for all rows of the row-by-row time variation noise average values;
   a time variation noise third calculating unit for calculating time variation noises for the respective rows by subtracting the time variation noise aggregate average value from the row-by-row time variation noise average values; and a time variation noise removing unit for subtracting the time variation noises for respective corresponding rows from the main pixel detection signals.

3. The light or radiation image pickup apparatus according to claim 1, wherein the image processor includes:

an offset signal removing unit for removing offset signals from the main pixel detection signals and the corrective voltage signals;

a time variation noise first calculating unit for calculating row-by-row time variation noise average values which are average values for each respective rows of the corrective signals with the offset signals removed therefrom;

a time variation noise second calculating unit for calculating a time variation noise block average value which is an average value for all rows from an nth row (n being a natural number) to an (n−m)th row (m being a natural number), from the row-by-row time variation noise average values acquired for respective rows from the nth row to the (n−m)th row;

a time variation noise third calculating unit for calculating a time variation noise for the nth row by subtracting the time variation noise block average value from the row-by-row time variation noise average value for nth row; and a time variation noise removing unit for subtracting the time variation noise for the nth row from the main pixel detection signals from the nth row;

the above signal processing being carried out successively for the nth row, an n+1th row, an n+2th row, and so on.

4. The light or radiation image pickup apparatus according to claim 3, wherein, when the (n−m) is a negative integer:

from row-by-row time variation noise average values acquired for respective rows from the nth row to a first row and from a row at a lower end of a preceding frame to an |n−m| th row from the lower end, the time variation noise second calculating unit calculates a time variation noise block average value which is an average value for all rows from the nth row to the first row and from the row at the lower end of the preceding frame to the |n−m| th row from the lower end;

the time variation noise third calculating unit calculates the time variation noise for the nth row by subtracting the time variation noise block average value from the row-by-row time variation noise average value for nth row; and the time variation noise removing unit subtracts the time variation noise for the nth row from the main pixel detection signals from the nth row;

the above signal processing being carried out successively for the nth row, an n+1th row, an n+2th row, and so on.

5. The light or radiation image pickup apparatus according to claim 1, wherein the reading device does not send the switching signal to the detecting elements arranged. in the corrective pixel area.

6. The light or radiation image pickup apparatus according to claim 1, wherein the corrective pixel area is disposed adjacent the main pixel area.

7. The light or radiation image pickup apparatus according to claim 6, wherein the corrective pixel area is disposed at one end of the radiation detecting device.

8. The light or radiation image pickup apparatus according to claim 7, wherein the corrective pixel area is disposed at opposite ends of the radiation detecting device.

* * * * *